US012806615B2

(12) United States Patent
Mashimo et al.

(10) Patent No.: US 12,806,615 B2
(45) Date of Patent: Nov. 24, 2026

(54) BIOSENSOR AND METHOD OF MANUFACTURING BIOSENSOR

(71) Applicant: ARKRAY, Inc., Kyoto (JP)

(72) Inventors: Taro Mashimo, Kyoto (JP); Shinjiro Sekimoto, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 632 days.

(21) Appl. No.: 18/137,114

(22) Filed: Apr. 20, 2023

(65) Prior Publication Data

US 2023/0338945 A1 Oct. 26, 2023

(30) Foreign Application Priority Data

Apr. 21, 2022 (JP) ................................ 2022-070371
Apr. 11, 2023 (JP) ................................ 2023-064395

(51) Int. Cl.
*B01L 1/00* (2006.01)
*B01L 3/00* (2006.01)
(Continued)

(52) U.S. Cl.
CPC ............ *B01L 3/5023* (2013.01); *C12Q 1/006* (2013.01); *C12Q 1/32* (2013.01); *B01L 2200/04* (2013.01);
(Continued)

(58) Field of Classification Search
None
See application file for complete search history.

(56) References Cited

U.S. PATENT DOCUMENTS 5,378,638 A * 1/1995 Deeg ................ G01N 33/54386 436/514
9,829,459 B2 11/2017 Zhu et al.
(Continued)

FOREIGN PATENT DOCUMENTS

EP 2554982 A1 2/2013
JP H6-3317 A 1/1994
(Continued)

OTHER PUBLICATIONS

Extended European Search Report dated Sep. 18, 2023, issued in corresponding European Patent Application No. 23169186.6.
(Continued)

*Primary Examiner* — Jyoti Mutreja
(74) *Attorney, Agent, or Firm* — Morgan, Lewis & Bockius LLP

(57) ABSTRACT

In one aspect, a biosensor that is capable of performing measurement with a high reproducibility, and a method of manufacturing the biosensor are provided. The present disclosure, as one aspect, relates to a biosensor that comprises a base material, a conductive part including two or more electrodes provided on a surface of the base material, and a reagent layer provided on at least a part of the conductive part, wherein the reagent layer is a reagent layer with the reagent stacked three-dimensionally, obtained by repeatedly forming droplet dots of the reagent on the conductive part. The present disclosure, as another aspect, relates to a method of manufacturing a biosensor that comprises a base material, a conductive part including two or more electrodes provided on a surface of the base material, and a reagent layer provided on at least a part of the conductive part, wherein the method comprises repeatedly forming droplet dots of a reagent on the conductive part to form the reagent layer in which the reagent is stacked three-dimensionally.

17 Claims, 6 Drawing Sheets

(51) Int. Cl.
*C12Q 1/00* (2006.01)
*C12Q 1/32* (2006.01)

(52) U.S. Cl.
CPC ....... *B01L 2200/12* (2013.01); *B01L 2200/16* (2013.01); *B01L 2300/0645* (2013.01); *B01L 2300/069* (2013.01)

(56) References Cited

U.S. PATENT DOCUMENTS

| | | | | |
|---|---|---|---|---|
| 2009/0035795 | A1 | 2/2009 | Dudenhoefer et al. | |
| 2012/0122197 | A1 | 5/2012 | Jospeh | |
| 2012/0150005 | A1 | 6/2012 | Hoss et al. | |
| 2013/0020196 | A1 | 1/2013 | Nishiwaki et al. | |
| 2013/0098775 | A1* | 4/2013 | Pei | C12Q 1/006 205/777.5 |
| 2014/0373347 | A1 | 12/2014 | Takagi | |
| 2015/0201491 | A1 | 7/2015 | Tatsuta | |
| 2016/0017399 | A1 | 1/2016 | Cardosi et al. | |

FOREIGN PATENT DOCUMENTS

| | | | |
|---|---|---|---|
| JP | 2011-99693 | A | 5/2011 |
| JP | 2017-520773 | A | 7/2017 |
| WO | 2016/009018 | A1 | 1/2016 |

OTHER PUBLICATIONS

Office Action issued in corresponding European Patent Application No. 23169186.6, dated Jul. 29, 2025.

* cited by examiner

BIOSENSOR AND METHOD OF MANUFACTURING BIOSENSOR

BACKGROUND

Technical Field

The present disclosure relates to a biosensor and a method of manufacturing the biosensor.

Background Art

A biosensor is a molecular measuring device using a molecule recognition element of a detection unit in which a biological material, such as an enzyme is arranged and a transducer (signal conversion device), such as electrodes. The biosensor is used for measuring various biological substances to be analyzed, such as glucose in a living body.

The biosensor generally includes electrodes and a reagent layer mounted on the electrodes. As a method of forming a reagent layer, an exemplary method is a method of applying a reagent liquid containing an oxidoreductase, an electron transfer substance and the like over the electrodes and drying the reagent liquid. Exemplary methods for applying a reagent liquid include the following: the dipping method, the dispenser method, screen process printing, offset printing, and ink-jet printing (JP-A-2011-99693, JP-A-H6 (1994)-3317, and JP-A-2017-520773).

SUMMARY

In the measurement of a variety of biological substances, such as glucose, using a biosensor, measurement with a higher accuracy (reproducibility) is required.

The present inventors found that irregularities in the concentration or amount of a reagent in a reagent layer cause irregularities in the dissolution of the reagent, and then lead to the deterioration of the reproducibility. A reagent layer is generally formed by applying a reagent liquid and drying the same. Precipitation occurs in peripheral parts of the reagent layer due to a concentration gradient that occurs in the process of drying, growing from crystals in the peripheral parts. The present inventors found that deviations in the timing of precipitation of components, occurring upon the formation of the reagent layer (particularly during drying), cause uneven drying, and as a result cause irregularities in the concentrations and amounts of reagent components in the reagent layer. Another method of forming a reagent layer by dispensing a single drop of reagent liquid only is also known. In this case, however, the amount of the reagent is greater in the peripheral part, while the amount of the reagent is smaller in the center part, which causes irregularities in the concentration or amounts of components such as an oxidoreductase in the reagent layer. This has been also found by the present inventors.

The present disclosure provides a biosensor that is capable of performing measurement with a high reproducibility, and a method that is capable of manufacturing a biosensor that is capable of performing measurement with a high reproducibility.

The present disclosure, as one aspect, relates to a biosensor that comprises a base material, a conductive part including two or more electrodes provided on a surface of the base material, and a reagent layer provided on at least a part of the conductive part, wherein the reagent layer is a reagent layer with the reagent stacked three-dimensionally, obtained by repeatedly forming droplet dots of the reagent on the conductive part.

The present disclosure, as another aspect, relates to a method of manufacturing a biosensor that comprises a base material, a conductive part including two or more electrodes provided on a surface of the base material, and a reagent layer provided on at least a part of the conductive part, the method comprising repeatedly forming droplet dots of a reagent on the conductive part to form the reagent layer in which the reagent is stacked three-dimensionally.

With the present disclosure, a biosensor that is capable of performing measurement with a high reproducibility can be provided, as can a method that is capable of manufacturing a biosensor that is capable of performing measurement with a high reproducibility.

DETAILED DESCRIPTION

Figure 1:
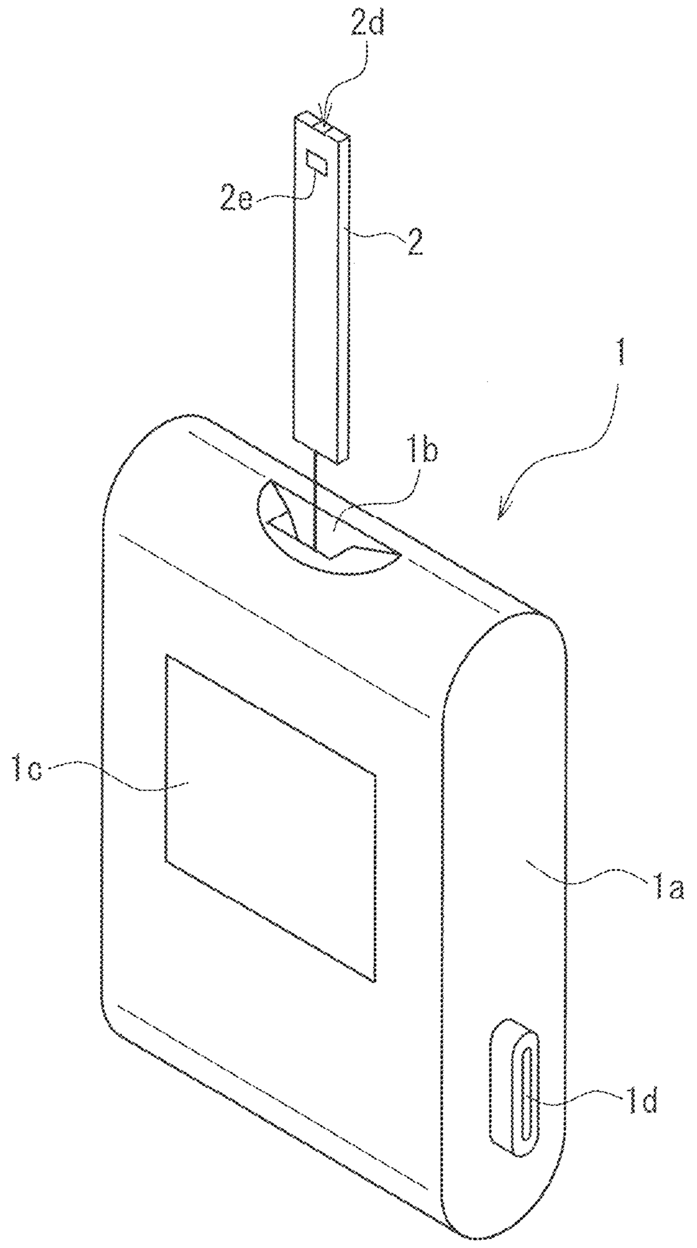
FIG. 1 is a perspective view illustrating an appearance of a biosensor in one embodiment of the present disclosure and a measurement device in which the biosensor is used.

The present inventors found that irregularities in the concentration or amount of a reagent in a reagent layer cause irregularities in the dissolution of the reagent, and then lead to the deterioration of the reproducibility. In the course of earnest research with a view to reducing the occurrence of the irregularities, the present inventors found that the repeated formation of droplet dots of a reagent on the conductive part to form a reagent layer with the reagent stacked three-dimensionally makes it possible to reduce uneven drying caused by deviations in the timing of precipitation of the reagent, which can occur upon the formation of the reagent layer, thereby reducing irregularities in the concentrations or amounts of the reagent components in the reagent layer.

JP-A-2011-99693 discloses a method of forming a reagent layer by spraying a reagent over surfaces of electrodes so that droplets of the reagent are separated from one another in order to avoid the occurrence of deviation of the amount of an enzyme caused by union of droplets. The method disclosed in JP-A-2011-99693 arranges droplets so that they are separated, thereby when the method is used for a biosensor in which a sufficient amount of a reagent has to be mounted within a limited range, there is the problem that a sufficient amount of a reagent cannot be mounted thereon.

By a new method found by the present inventors, the formation of droplet dots of a reagent is repeated so that the reagent is three-dimensionally stacked, which makes it possible to mount a sufficient amount of the reagent required for measuring a biological substance on a biosensor.

Method of Manufacturing Biosensor

The present disclosure, as one aspect, relates to a method of manufacturing a biosensor that includes a base material, a conductive part including two or more electrodes formed on a surface of the base material, and a reagent layer mounted on at least a part of the conductive part. The method of the present disclosure includes repeatedly forming droplet dots of a reagent on the conductive part to form the reagent layer in which the reagent is stacked three-dimensionally.

With the method of the present disclosure, in one or a plurality of embodiments, a biosensor that is capable of performing the measurement with a high reproducibility can be manufactured. With the method of the present disclosure, in one or a plurality of embodiments, lot-to-lot differences and within-lot differences can be reduced, which makes it possible to output a correct response-measured value, thereby providing a biosensor that is capable of providing an accurate value.

The "droplet dots of a reagent" in the present disclosure refers to dot-form droplets formed with a reagent liquid, in a state before drying (in a liquid state). In one or a plurality of embodiments, the "droplet dots of a reagent" refers to droplet dots that are ejected from an ejection head of a printing device and adhere to an object (the conductive part, etc.) in a state before drying. In one or a plurality of embodiments, the "droplet dots of a reagent" can encompass droplet dots formed with the same reagent, and droplet dots formed with different reagents. In the present disclosure, in one or a plurality of embodiments, the "different reagents" can encompass reagents including different compositions, reagents that have the same composition but different composition ratios, and reagents that have the same composition and the same composition ratios, but different concentrations.

The "reagent layer with the reagent stacked three-dimensionally" in the present disclosure refers to a reagent layer that is obtained by accumulation of reagent components thereby becoming a thick, three-dimensional shape. In one or a plurality of embodiments, the "reagent layer with the reagent stacked three-dimensionally" is a reagent layer in which the reagent is stacked three-dimensionally. In one or a plurality of embodiments, the "reagent layer with the reagent stacked three-dimensionally" is a reagent layer obtained by stacking droplet dots of a reagent and then drying the same on the conductive part. In one or a plurality of embodiments, an exemplary reagent layer with the reagent stacked three-dimensionally is a reagent layer formed with an accumulated dried reagent, obtained by repeatedly dispensing a droplet of a reagent to form droplet dots of the reagent on a layer formed with dried droplet dots of the reagent, and drying the droplet dots.

Figure 6:
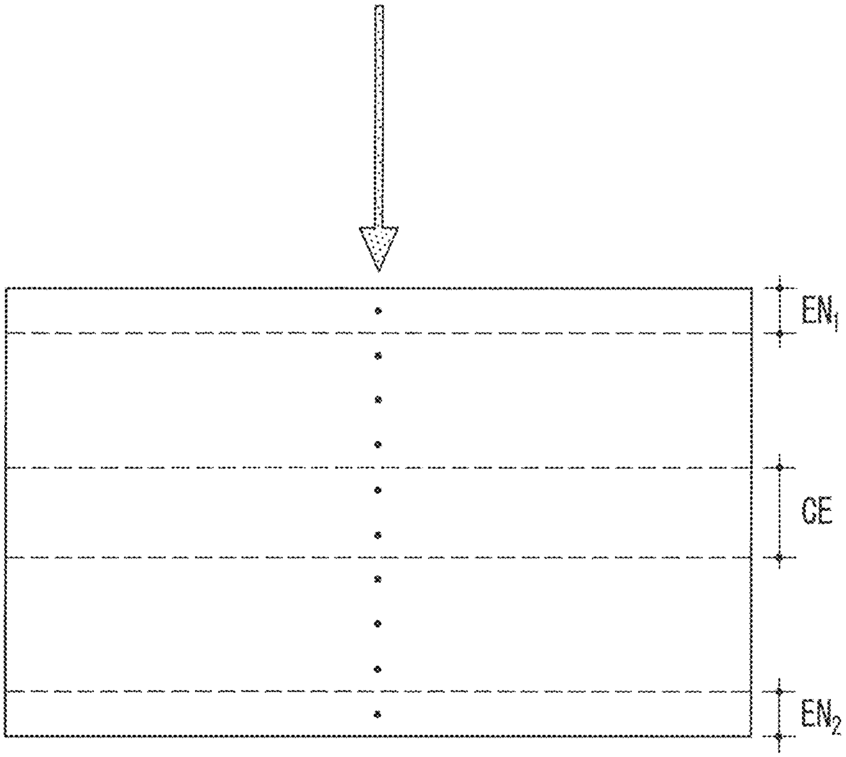
FIG. 6 is a schematic diagram for explaining measurement of the thickness of the reagent layer in the example.

In one or a plurality of embodiments, the reagent layer has a mean thickness of 5 μm to 10 μm. The mean thickness of the reagent layer is above 5 μm, preferably 6 μm or more, 6.5 μm or more, or 7 μm or more, from the viewpoint of obtaining a higher reproducibility. The mean thickness of the reagent layer is 9.5 μm or less, preferably 9 μm or less, or 8.5 μm or less, from the same viewpoint. The mean thickness of the reagent layer can be measured and calculated by the method described in the Example. The measurement of the thickness of the reagent layer can be performed by, for example, measuring the thickness thereof along the center line directed along the traverse direction of the reagent layer (the position indicated by the arrow in FIG. 6), as described in the Example. FIG. 6 is a schematic diagram for explaining a method of measuring a mean thickness of the reagent layer, in which only the reagent layer is focused and shown. Incidentally, the reagent layer in the present disclosure refers to a layer of a reagent mounted in an area that is substantially involved in the measurement of an analysis object. Examples of the area that is substantially involved in the measurement of an analysis object include the inside of a flow channel in which a sample flows, in one or a plurality of embodiments.

The method of the present disclosure includes repeatedly forming droplet dots of a reagent on the conductive part to form a reagent layer with the reagent stacked three-dimensionally on the conductive part. In one or a plurality of embodiments, the reagent layer may contain reagent components other than the oxidoreductase and the electron transfer substance. Examples of the other reagent components include a buffer, an amino acid, a surfactant, and a binder, in one or a plurality of embodiments.

In one or a plurality of embodiments, the droplet dots can be formed by ejecting a reagent liquid containing reagent components. In one or a plurality of embodiments, the ejected amount for a reagent can be appropriately determined depending on the pitch of the positions where droplet dots are formed (positions where droplets are ejected), the size of the droplet dot to be formed, and the like. In one or a plurality of embodiments, the ejected amount for a reagent is 10 ng to 30 ng per one droplet dot, and from the viewpoint of further reducing irregularities in the concentrations and amounts of reagent components in the reagent layer and further enhancing the reproducibility of the measurement accuracy of a biosensor to be obtained, the foregoing amount is 12 ng to 25 ng, or 12 ng to 15 ng.

In one or a plurality of embodiments, the ejected amount for a reagent per one droplet dot may be different between the first layer and the subsequent layers. From the viewpoint of further reducing irregularities in the concentrations and amounts of reagent components in the reagent layer, and further enhancing the reproducibility of the measurement accuracy of a biosensor to be obtained, the ejected amount for a reagent for the second or subsequent layer is preferably greater than the ejected amount for a reagent for the first layer. In one or a plurality of particularly non-limiting embodiments, for example, the ejected amount for a reagent for the first layer is set to less than 20 ng per one droplet dot, and the ejected amount for a reagent for the second or subsequent layer is set to 20 ng or more per one droplet dot. In one or a plurality of embodiments, the ejected amount for a reagent for the first layer is 10 ng to 18 ng per one droplet dot, and from the viewpoint of further reducing irregularities in the concentrations and amounts of reagent components in the reagent layer, and further enhancing the reproducibility of the measurement accuracy of a biosensor to be obtained, the foregoing amount is preferably 11 ng or more. From the same viewpoint, the foregoing amount is preferably 17 ng or less, 15 ng or less, 14 ng or less, or 13 ng or less. In one or a plurality of embodiments, the ejected amount for a reagent for the second or subsequent layer is 20 ng to 28 ng per one droplet dot, and from the viewpoint of further reducing irregularities in the concentrations and amounts of reagent components in the reagent layer, and further enhancing the reproducibility of the measurement accuracy of a biosensor to be obtained, the foregoing amount is preferably 21 ng or more. From the same viewpoint, the foregoing amount is preferably 26 ng or less, 25 ng or less, or 24 ng or less. In one or a plurality of embodiments, the ejected amount for a reagent per one droplet dot for the second or subsequent layer may be the same or different.

The method of the present disclosure, in one or a plurality of embodiments, includes drying droplet dots of the reagent. In one or a plurality of embodiments, the drying method is not particularly limited, and it is, for example, a method of leaving at room temperature, drying with warm air or the like, leaving under high temperature conditions or the like. From the viewpoint of further reducing irregularities in the concentrations and amounts of reagent components in the reagent layer, and further enhancing the reproducibility of the measurement accuracy of a biosensor to be obtained, drying at room temperature is preferred. The time for drying can be appropriately determined depending on the amount ejected for a droplet, drying conditions, and the like; and the longer the time the more preferable, from the viewpoint of further reducing reagent irregularities. In one or a plurality of embodiments, the drying time is 10 seconds or more or 15 seconds or more, and from the viewpoint of further reducing irregularities in the concentrations and amounts of reagent components in the reagent layer and further enhancing the reproducibility of the measurement accuracy of a biosensor to be obtained, it is 20 seconds or more, 25 seconds or more, or 30 seconds or more. The upper limit of the drying time is not limited particularly, and in one or a plurality of embodiments, the drying time is 120 seconds or less, or 90 seconds or less. From the viewpoint of further reducing irregularities in the concentrations and amounts of reagent components in the reagent layer, and further enhancing the reproducibility of the measurement accuracy of a biosensor to be obtained, an exemplary drying condition is, for example, a humidity of 50% or less.

In one or a plurality of embodiments, the method of the present disclosure includes forming droplet dots of a reagent for the Nth layer (N is a natural number of 1 or greater) at predetermined pitches, and forming droplet dots of a reagent for the (N+1)th layer on the dried droplet dots of the Nth layer. In one or a plurality of embodiments, N is a natural number of 1, 2, 3, 4, 5, 6, 7, 8, 9, 10, or greater.

From the viewpoint of further reducing irregularities in the concentrations and amounts of reagent components in the reagent layer and further enhancing the reproducibility of the measurement accuracy of a biosensor to be obtained, the method of the present disclosure includes repeating the formation of droplet dots of a reagent until droplet dots of at least the fourth layer are formed.

In one or a plurality of embodiments, the droplet dots may be formed with the same reagent, or may be formed with a plurality of types, i.e., two or more, of different reagents including different compositions. In one or a plurality of particularly non-limiting embodiments, the method of the present disclosure includes forming droplet dots for the first layer and droplet dots for the second layer, using different reagents from each other, respectively. In one or a plurality of particularly non-limiting embodiments, the method of the present disclosure includes forming droplet dots for an odd-numbered layer and droplet dots for an even-numbered layer, using different reagents from each other, respectively.

In one or a plurality of embodiments, the method of the present disclosure includes a step for drying droplet dots, between the step of forming droplet dots for the Nth layer and the step of forming droplet dots for the (N+1)th layer. In a case where the formation of droplet dots for the Nth layer and the formation of droplet dots for the (N+1)th layer are carried out by different ejection devices, the time for carrying the base material may be the time for drying the droplet dots.

In one or a plurality of embodiments, the pitch at which the droplet dots of a reagent are formed (the distance between the centers of adjacent droplet dots) is 50 μm to 150 μm. From the viewpoint of further reducing irregularities in the concentrations and amounts of reagent components in the reagent layer, and further enhancing the reproducibility of the measurement accuracy of a biosensor to be obtained, the pitch is preferably 60 μm to 80 μm, and more preferably 65 μm to 75 μm. In one or a plurality of embodiments, the "center of a droplet dot" in the present disclosure refers to the center of a circle that, after a droplet dot of a reagent is formed on the conductive part and is dried, circumscribes the circumference of the dried droplet dot.

In one or a plurality of embodiments, the pitches at which the droplet dots are formed may be fixed pitches or variable pitches. From the viewpoint of further reducing irregularities in the concentrations and amounts of reagent components in the reagent layer and further enhancing the reproducibility of the measurement accuracy of a biosensor to be obtained, the pitches are preferably fixed pitches.

In one or a plurality of embodiments, the pitches at which the droplet dots of a reagent are formed may be different or the same between the layers. From the viewpoint of further reducing irregularities in the concentrations and amounts of reagent components in the reagent layer and further enhancing the reproducibility of the measurement accuracy of a biosensor to be obtained, the pitches are preferably the same between the layers.

The formation of droplet dots of a reagent for the first layer is performed in such a manner that adjacent droplet dots do not overlap, from the viewpoint of preventing from uniting into one greater droplet on the base material or the conductive part, further reducing irregularities in the concentrations and amounts of reagent components in the reagent layer and further enhancing the reproducibility of the measurement accuracy of a biosensor to be obtained. In the present disclosure, in one or a plurality of embodiments, "adjacent droplet dots do not overlap" means, for example, that adjacent droplet dots do not unite to form one droplet dot, or that an ejected droplet becomes an independent droplet dot.

In one or a plurality of embodiments, the method of the present disclosure may include controlling an amount of a reagent ejected for forming droplet dots of a reagent, in the formation of droplet dots of the reagent for the first layer. The ejected amount for a reagent per one droplet dot for the first layer can be appropriately determined depending on the pitch at which the droplet dots are formed (the distance between the centers of adjacent droplet dots) and the size of the droplet dot to be formed. In one or a plurality of embodiments, the amount of ejected reagent is 10 ng to 18 ng per one droplet dot, in the formation of droplet dots for the first layer, and from the viewpoint of further reducing irregularities in the concentrations and amounts of reagent components in the reagent layer, and further enhancing the reproducibility of the measurement accuracy of a biosensor to be obtained, the foregoing amount is preferably 11 ng to 15 ng, and more preferably 11 ng to 13 ng.

In one or a plurality of embodiments, the size of the dried droplet dot for the first layer is 30 μm to 90 μm. From the viewpoint of further reducing irregularities in the concentrations and amounts of reagent components in the reagent layer and further enhancing the reproducibility of the measurement accuracy of a biosensor to be obtained, the foregoing size is preferably 40 μm to 80 μm, and more preferably 50 μm to 70 μm. In the present disclosure, "the size of the dried droplet dot" refers to the longest diameter of the droplet dot after drying. The size of the droplet dot after drying can be measured by the method described in the Example.

In one or a plurality of embodiments, the dried droplet dots for the first layer have a density of 0.86 $\mu g/\mu m^2$ to 1.7 $\mu g/\mu m^2$. The density of the dried droplet dots can be determined by calculating the solid compound in the droplets and the area of the dried dots formed after drying.

The formation of droplet dots of the reagent for the second or subsequent layer is preferably performed so that adjacent droplet dots of a reagent abut one another, from the viewpoint of further reducing irregularities in the concentrations and amounts of reagent components in the reagent layer and further enhancing the reproducibility of the measurement accuracy of a biosensor to be obtained. In the present disclosure, in one or a plurality of embodiments, "adjacent droplet dots abut one another" means, for example, that adjacent droplet dots of a reagent can unite to form one droplet dot of a reagent, that adjacent dried droplet dots overlap partially, or that adjacent dried droplets are continuous to one another.

In one or a plurality of embodiments, the formation of droplet dots of the reagent for the second layer is performed, for example, so that an entirety of an area where the reagent layer is to be formed is covered with the reagent (droplet dots of the reagent).

In one or a plurality of embodiments, the method of the present disclosure may include controlling an amount of a reagent ejected for forming droplet dots of a reagent, in the formation of droplet dots of the reagent for the second or subsequent layer (the (N+1)th layer).

The ejected amount for a reagent per one droplet dot for the (N+1)th layer can be appropriately determined depending on the pitch at which the droplet dots are formed (the distance between the centers of adjacent droplet dots) and the size of the droplet dot to be formed. In one or a plurality of embodiments, the ejected amount for a reagent is 20 ng to 28 ng per one droplet dot, in the formation of droplet dots for the (N+1)th layer, and from the viewpoint of further reducing irregularities in the concentrations and amounts of reagent components in the reagent layer, and further enhancing the reproducibility of the measurement accuracy of a biosensor to be obtained, the foregoing amount is preferably 21 ng to 25 ng, and more preferably 21 ng to 24 ng. In one or a plurality of embodiments, the ejected amount for a droplet for the second or subsequent layer (the (N+1)th layer) may be the same or different.

In one or a plurality of embodiments, the size of the dried droplet dot for the second or subsequent layer (the (N+1)th layer) is 80 μm to 120 μm. From the viewpoint of further reducing irregularities in the concentrations and amounts of reagent components in the reagent layer and further enhancing the reproducibility of the measurement accuracy of a biosensor to be obtained, the foregoing size is preferably 85 μm to 110 μm, and more preferably 90 μm to 100 μm. In one or a plurality of embodiments, the size of the dried droplet dot for the second or subsequent layer (the (N+1)th layer) may be the same or different.

Figure 4:
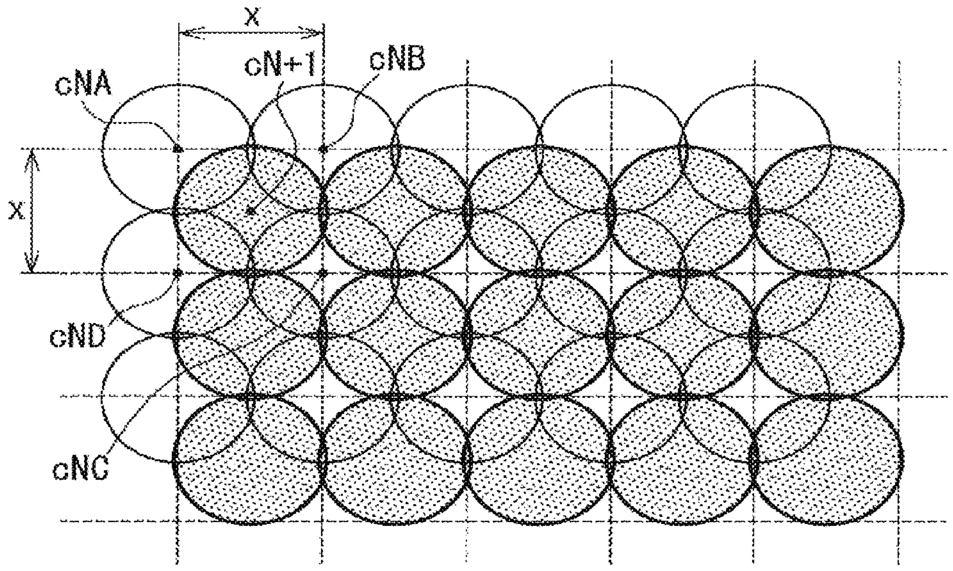
FIG. 4 is a schematic diagram for explaining a method of forming a reagent layer in an example.

In one or a plurality of particularly non-limiting embodiments in the present disclosure, the formation of droplet dots of the reagent for the (N+1)th layer can be performed so that the center of each of the foregoing droplet dots is positioned at a point of intersection of lines extended between the centers of adjacent droplet dots in the Nth layer, from the viewpoint of further reducing irregularities in the concentrations and amounts of reagent components in the reagent layer and further enhancing the reproducibility of the measurement accuracy of a biosensor to be obtained. In one or a plurality of embodiments, the "point of intersection of line extended between the centers of adjacent droplet dots in the Nth layer" in the present disclosure is, for example, a point of intersection of diagonal lines of a quadrangle having the centers of four adjacent droplet dots as its vertices. In one or a plurality of particularly non-limiting embodiments, the foregoing point is, for example, cN+1 in FIG. 4 (a point of intersection of diagonal lines of a quadrangle having the four centers (cNA, cNB, cNC, and cND) of droplet dots as its vertices).

The formation of droplet dots of the reagent for the (N+1)th layer is preferably performed so that the droplet dots of the reagent formed for the (N+1)th layer at least partially cover the dried droplet dots of the Nth layer, from the viewpoint of further reducing irregularities in the concentrations and amounts of reagent components in the reagent layer and further enhancing the reproducibility of the measurement accuracy of a biosensor to be obtained.

In one or a plurality of embodiments, the formation of the reagent layer is performed preferably using the ink-jet method. In one or a plurality of embodiments, the formation of droplet dots of a reagent can be performed using a device having a nozzle that is capable of ejecting a small amount of reagent such as an ink-jet printer.

The size of the reagent layer may be appropriately determined according to the shapes of the base material, the flow channel, the conductive part, and the like. When the base material is in a rectangular shape having a width of 7 mm and a length of 30 mm, the flow channel is in a rectangular shape having a width of 1.8 mm and a length of 4 mm, and a part of a working electrode of the conductive part exposed in the flow channel is in a rectangular shape having a width of 1.8 mm and a length of 0.8 mm, the reagent layer has a length (a length in the widthwise direction of the biosensor) of 1.5 mm or more, 2 mm or more, 2.5 mm or more, or 3 mm or more, in one or a plurality of embodiments. The length of the reagent layer (the length in the widthwise direction of the biosensor) is 5 mm or less, 4.5 mm or less, or 4 mm or less, in one or a plurality of embodiments. The reagent layer has a width (a length in the longitudinal direction of the biosensor) of 0.5 mm or more, 0.6 mm or more, 0.8 mm or more, or 0.9 mm or more in one or a plurality of embodiments. The width of the reagent layer (the length in the longitudinal direction of the biosensor) is 2 mm or less, 1.6 mm or less, or 1.4 mm or less, in one or a plurality of embodiments.

Biosensor

The present disclosure, as one aspect, relates to a biosensor that includes a base material, a conductive part including two or more electrodes formed on a surface of the base material, and a reagent layer mounted on at least a part of the conductive part. The reagent layer in the biosensor of the present disclosure is a reagent layer with the reagent stacked three-dimensionally, obtained by repeatedly forming droplet dots of a reagent on the conductive part. The biosensor of the present disclosure is, as another aspect, a biosensor manufactured by the method of the present disclosure.

With the biosensor of the present disclosure, in one or a plurality of embodiments, the measurement with a high reproducibility can be performed. With the biosensor of the present disclosure, in one or a plurality of embodiments, lot-to-lot differences and within-lot differences can be reduced, which makes it possible to output a correct response-measured value, thereby providing an accurate value.

In one or a plurality of embodiments, the reagent layer has a mean thickness of 5 μm to 10 μm. The mean thickness of the reagent layer is above 5 μm, preferably 6 μm or more, 6.5 μm or more, or 7 μm or more, from the viewpoint of obtaining a higher reproducibility. The mean thickness of the reagent layer is 9.5 μm or less, preferably 9 μm or less, or 8.5 μm or less, from the same viewpoint. The mean thickness of the reagent layer can be measured and calculated by the method described in the Example.

In one or a plurality of embodiments, the difference between a mean thickness of a peripheral part and a mean thickness of a central part in the reagent layer (also referred to as a "difference between thicknesses of the peripheral and central parts") is −6 μm to +5 μm. The difference between thicknesses of the peripheral and central parts is preferably −5 μm to +5 μm, −4 μm to +4 μm, −3 μm to +3 μm, −2 μm to +2 μm, or −1 μm to +1 μm, from the viewpoint of obtaining a higher reproducibility. From the same viewpoint, the difference between mean thicknesses of the peripheral and central parts is more preferably −3.5 μm to +2.5 μm, −3 μm to +2 μm, or −3 μm to +1.5 μm. The difference between a mean thickness of a peripheral part and a mean thickness of a central part in the reagent layer can be calculated by the method described in the Example.

The mean thickness of the central part and the mean thickness of the peripheral part in the reagent layer can be calculated using thicknesses measured in the same method as that used for the mean thickness of the reagent layer, as in the method described in the Example.

[Shape of Reagent Layer: Prismatic Column (Rectangular Parallelepiped)]

When the reagent layer has a shape of a prismatic column (rectangular parallelepiped) or another similar shape, the mean thickness of the central part in the reagent layer may be assumed to be a mean value of thicknesses in a range with a width of 0.1 mm on each side in a traverse direction from a point of intersection of a traverse-direction center line and a longitudinal-direction center line of the reagent layer (a range with a width of 0.2 mm in total, for example, a range CE in FIG. 6). In a case where, in a biosensor in which a flow channel through which a sample flows is formed on a base material, the reagent layer is mounted in the flow channel, the traverse direction of the reagent layer is a direction of a flow channel in which the sample flows, and the longitudinal direction of the reagent layer is a widthwise direction of the biosensor that is orthogonal to the flow channel direction (for example, in the aspect illustrated in FIG. 2), the mean thickness of the central part in the reagent layer can be paraphrased as a mean value of thicknesses in a range with a width of 0.1 mm on each of the upstream side and the downstream side from the point of intersection of the transverse-direction center line and the longitudinal-direction center line of the reagent layer (a range with a width of 0.2 mm in total).

When the reagent layer has a shape of a prismatic column, the mean thickness of the peripheral part in the reagent layer refers to a mean value of thicknesses in a range with a width of 0.1 mm from each end of the reagent layer in the traverse direction (for example, ranges EN1 and EN2 in FIG. 6).

[Shape of Reagent Layer: Circular Column]

When the reagent layer has a shape of a circular column or another similar shape, the mean thickness of the central part in the reagent layer refers to a mean value of thicknesses in a range with a width of a radius of 0.1 mm from the center of the reagent layer in the longitudinal direction of the biosensor. The mean thickness of the peripheral part refers to a mean value of thicknesses in a range with a width of 0.1 mm from the circumference, which is a mean value of thicknesses in a range with a width of 0.1 mm from each end (circumference) of the reagent layer (width of 0.1 mm×2) in the center line of the reagent layer parallel to the longitudinal direction of the biosensor.

The respective mean thickness of the central part and the mean thickness of the peripheral part of the reagent layer can be measured and calculated by the method described in the Example.

In one or a plurality of embodiments, examples of the shape of the reagent layer as viewed from above the top surface include a circular shape, an elliptical shape, and a polygonal shape. In one or a plurality of embodiments, examples of the polygonal shape include a triangle, a quadrangle, a pentagon, a hexagon, a heptagon, and an octagon. In one or a plurality of embodiments, the reagent layer can be referred to as a columnal structure. In one or a plurality of embodiments, the reagent layer may be in a prismatic column shape, a circular column shape, or an elliptical column shape. In one or a plurality of embodiments, the reagent layer is in a rectangular column shape, and preferably in an approximate rectangular parallelepiped shape. In one or a plurality of embodiments, when the reagent layer is in an approximate rectangular parallelepiped shape, the reagent layer is arranged on a base material in such a manner that the longitudinal direction of the reagent layer intersects at right angles with the longitudinal direction of the biosensor.

In one or a plurality of embodiments, the reagent layer in the biosensor of the present disclosure contains an oxidoreductase and an electron transfer substance.

[Oxidoreductase]

Examples of the oxidoreductase, in one or a plurality of embodiments, include glucose dehydrogenase (GDH), glucose oxidase (GOD), cholesterol oxidase, quinohaemoprotein ethanol dehydrogenase (QHEDH (PQQ Ethanol dh)), sorbitol dehydrogenase, D-fructose dehydrogenase, D-glucoside-3-dehydrogenase, cellobiose dehydrogenase, lactate oxidase (LOD), lactate dehydrogenase (LDH), and urinate dehydrogenase.

The oxidoreductase, in one or a plurality of embodiments, may include flavin adenine dinucleotide (FAD), pyrroloquinoline quinone (PQQ), nicotinamide adenine dinucleotide (NAD), or nicotinamide adenine dinucleotide phosphate (NADP), as a co-enzyme (also referred to as a catalyst sub-unit, or a catalyst domain). In one or a plurality of embodiments, examples of the oxidoreductase containing a co-enzyme include FAD-GDH, PQQ-GDH, NAD-GDH, and NADP-GDH.

Examples of the oxidoreductase, in one or a plurality of embodiments, include Aspergillus oryzae-type FAD-GDH (flavin adenine dinucleotide-dependent glucose dehydrogenase, or flavin adenine dinucleotide-linked glucose dehydrogenase). As the Aspergillus oryzae-type FAD-GDH, in one or a plurality of embodiments, those disclosed in JP-A-

2013-083634 can be used. The contents of the foregoing document are incorporated herein by reference as a part of the present disclosure.

In one or a plurality of embodiments, the amount of the oxidoreductase in the reagent layer is 1000 KU/$cm^3$ or less, preferably 500 KU/$cm^3$ or less, and more preferably 300 KU/$cm^3$ or less. The lower limit of the amount of the oxidoreductase in the reagent layer is not particularly limited, and is 1 KU/$cm^3$ or more, in one or a plurality of embodiments. In one or a plurality of embodiments, the amount of the oxidoreductase in the reagent layer is 200 KU/$cm^3$ to 300 KU/$cm^3$, preferably 200 KU/$cm^3$ to 280 KU/$cm^3$, and more preferably 210 KU/$cm^3$ to 260 KU/$cm^3$. In the present disclosure, "U" is a unit of an enzyme activity and refers to an amount of an enzyme that reacts with 1 μmol of a substrate during 1 minute under optimum conditions. In the present disclosure, "KU" means a kilo unit (kilo U).

[Electron Transfer Substance]

In one or a plurality of embodiments, examples of the electron transfer substance include ruthenium compounds, 1-methoxy-PES (1-Methoxy-5-ethylphenazinium ethylsulfate, 1-mPES), 1-methoxy-PMS (1-Methoxy-5-methylphenazinium methylsulfate, 1-mPMS), phenylenediamine compounds, quinone compounds, ferricyanide compounds, Coenzyme Q0 (2,3-Dimethoxy-5-methyl-p-benzoquinone), AZURE A Chloride (3-amino-7-(dimethylamino)phenothiazin-5-ium chloride), Phenosafranin, 6-Aminoquinoxaline (3,7-Diamino-5-phenylphenanzinium chloride), and Tetrathiafulvalene.

As the ruthenium compound, in one or a plurality of embodiments, a ruthenium compound that is present in a reaction system as an oxide-type ruthenium complex and functions as an electron transfer substance can be used. The type of a ligand of the ruthenium complex is not limited particularly. In one or a plurality of embodiments, examples of the ruthenium compound include an oxide-type ruthenium complex expressed by the following chemical formula:

$$[Ru(NH_3)_5X]^{n+}.$$

X is, for example, $NH_3$, a halogen ion, CN, pyridine, nicotinamide, or $H_2O$, among which $NH_3$ or a halogen ion is preferable. In one or a plurality of embodiments, examples of the halogen ion include $Cl^-$, $F^-$, $Br^-$, and I. "n+" in the chemical formula represents a valence of oxide-type ruthenium (III) complex determined by the type of X. As the ruthenium complex, in one or a plurality of embodiments, those disclosed in JP-A-2018-013400 can be used. The contents of the foregoing document are incorporated herein by reference as a part of the present disclosure. In one or a plurality of embodiments, examples of the ruthenium compound include ruthenium hexamines such as $[Ru(NH_3)_6]^{2+}$ and $[Ru(NH_3)_6]^{3+}$. In one or a plurality of embodiments, examples of the ruthenium compound include $[Ru(NH_3)_6]Cl_3$.

In one or a plurality of embodiments, examples of the phenylenediamine compound include N,N-Dimethyl-1,4-phenylenediamine, and N,N,N',N'-tetramethyl-1,4-phenylenediaminedihydrochloride.

In one or a plurality of embodiments, examples of the quinone compound include 1,4-Naphthoquinone, 2-Methyl-1,4-Naphthoquinone (VK3), 9,10-Phenanthrenequinone, 1,2-Naphthoquinone, p-Xyloquinone, Methylbenzoquinone, 2,6-Dimethylbenzoquinone, Sodium1,2-Naphthoquinone-4-sulfonate, 1,4-Anthraquinone, Tetramethylbenzoquinone, and Thymoquinone.

In one or a plurality of embodiments, examples of the ferricyanide compound include calcium ferricyanide.

In one or a plurality of embodiments, the amount of the electron transfer substance in the reagent layer is 0.1 mmol/$cm^3$ or more, preferably 0.5 mmol/$cm^3$ or more, or more preferably 1 mmol/$cm^3$. The upper limit of the amount of the electron transfer substance in the reagent layer is not particularly limited, and is 50 mmol/$cm^3$ or less, or 10 mmol/$cm^3$ or less, in one or a plurality of embodiments.

The reagent layer may contain components other than the oxidoreductase and the electron transfer substance. Examples of the other components include a buffer, an amino acid, a surfactant, and a binder, in one or a plurality of embodiments.

In one or a plurality of embodiments, examples of the buffer include a phosphate buffer, an amine-based buffer, and a buffer having a carboxyl group. In one or a plurality of embodiments, examples of the amine-based buffer include Tris (tris(hydroxymethyl)aminomethane), ACES (N-(2-Acetamido)-2-aminoethanesulfonic acid), CHES (N-Cyclohexyl-2-aminoethanesulfonic acid), CAPSO (3-(Cyclohexylamino)-2-hydroxy-1-propanesulfonic acid), TAPS (N-Tris(hydroxymethyl)methyl-3-aminopropanesulfonic acid), CAPS (N-Cyclohexyl-3-aminopropanesulfonic acid), Bis-Tris (Bis(2-hydroxyethyl)iminotris(hydroxymethyl)methane), TAPSO (2-Hydroxy-N-tris (hydroxymethyl)methyl-3-aminopropanesulfonic acid), TES (N-Tris(hydroxymethyl)methyl-2-aminoethanesulfonic acid), Tricine (N-[Tris(hydroxymethyOmethyl]glycine), and ADA (N-(2-Acetamido)iminodiacetic acid). In one or a plurality of embodiments, examples of the buffer having a carboxyl group include a citrate buffer, a phosphate citrate buffer, an acetic acid-sodium acetate buffer, a malic acid-sodium acetate buffer, a malonic acid-sodium acetate buffer, and a succinic acid-sodium acetate buffer. As the buffer, one type may be used alone, or two or more types may be used in combination. In one or a plurality of embodiments, the pH of the buffer is 6.8 to 7.5, and preferably 6.9 to 7.0.

In one or a plurality of embodiments, examples of the amino acid include glycine, serine, lysin, and histidine.

In one or a plurality of embodiments, examples of the surfactant include TritonX-100 ((p-tert-octylphenoxy)polyethoxyethanol), Tween20 (polyoxyethylene sorbitan monolaurate), sodium dodecyl sulfate, perfluorooctanesulfonic acid, sodium stearate, alkylaminocarboxylic acid (or a salt of the same), carboxybetaine, sulfobetaine, and phosphobetaine. As the surfactant, one type may be used alone, or two or more types may be used in combination.

In one or a plurality of embodiments, examples of the binder include a resin binder and a layered inorganic compound. In one or a plurality of embodiments, examples of the resin binder include a butyral resin binder and a polyester resin compound binder. As the layered inorganic compound, the layered inorganic compounds disclosed in WO2005/043146 can be used. In one or a plurality of embodiments, examples of the layered inorganic compound include a swelling clay mineral having an ion exchange capacity. In one or a plurality of embodiments, examples of the layered inorganic compound include bentonite, smectite, vermiculite, and synthetic fluoromica. As the binder, one type may be used alone, or two or more types may be used in combination.

[Base Material]

In one or a plurality of embodiments, examples of the base material include an insulating base material (insulating substrate) in a sheet form. In one or a plurality of embodiments, examples of the material for the insulating substrate include thermoplastic resin, thermosetting resin, glass, ceramic, and paper. In one or a plurality of embodiments, examples of the thermoplastic resin include polyether-imide (PEI), polyethylene terephthalate (PET), and polyethylene (PE). In one or a plurality of embodiments, examples of the thermosetting resin include polyimide resin and epoxy resin.

[Conductive Part]

The conductive part includes two or more electrodes and is formed on a surface of the base material. In one or a plurality of embodiments, the electrodes may be an electrode pair that includes a working electrode and a counter-electrode, or may be a three-electrode system that includes a working electrode, a counter-electrode, and a reference electrode. In one or a plurality of embodiments, the conductive part may further include a detection electrode. In a case where the conductive part includes at least an electrode pair including a working electrode and a counter-electrode, the reagent layer is preferably mounted on at least the working electrode, in one or a plurality of embodiments.

As the material for the electrodes, in one or a plurality of embodiments, conductive materials can be used. In one or a plurality of embodiments, examples of the conductive material include metal materials and carbon materials. In one or a plurality of embodiments, examples of the metal material include gold (Au), platinum (Pt), silver (Ag), ruthenium (Ru), palladium (Pd), and nickel (Ni) alloys. In one or a plurality of embodiments, examples of the nickel alloy include nickel-vanadium alloy, nickel-tungsten alloy, and nickel-ruthenium alloy. In one or a plurality of embodiments, examples of the carbon material include graphite, carbon nanotube, graphene, and mesoporous carbon.

In one or a plurality of embodiments, examples of the electrode include a thin film electrode created by forming a film of the above-described material such as the metal material on a base material. In one or a plurality of embodiments, examples of the film-forming method include screen printing, physical vapor deposition (PVD, for example, sputtering), and chemical vapor deposition (CVD).

Examples of the sample in the biosensor of the present disclosure include a biological specimen in one or a plurality of embodiments. Examples of the biological specimen include blood, urine, and specimens derived from these, cell-extract specimens, and cell-culture solutions, in one or a plurality of embodiments.

Examples of the measurement object in the biosensor of the present disclosure, in one or a plurality of embodiments, include glucose, cholesterol, ethanol, sorbitol, fructose, cellobiose, lactic acid, and urea.

[Measuring Method]

The present disclosure relates to, as another aspect, a method of electrochemically measuring a measurement object in a sample using a biosensor of the present disclosure, comprising bringing a sample into contact with the reagent layer of the biosensor; applying a voltage across electrodes of the biosensor; and measuring an electric signal generated by the application of the voltage.

In the present disclosure, "electrochemically measuring" refers to measuring by applying electrochemical measurement techniques, and examples of the same include the amperometric method, the potential difference measuring method, and the coulometric analysis method, in one or a plurality of embodiments. In one or a plurality of embodiments, examples of the amperometric method include the method of measuring a value of electric current generated when a reduced electron transfer substance is oxidized by application of a voltage.

In one or a plurality of embodiments, the voltage to be applied is, although not particularly limited to, 10 mV or more, or 50 mV or more, and preferably 100 mV or more. In addition, in one or a plurality of embodiments, the voltage to be applied is, although not particularly limited to, 1000 mV or less, 700 mV or less, preferably 600 mV or less, 500 mV or less, 400 mV or less, or 300 mV or less.

Embodiment

An exemplary biosensor manufacturing method of the present disclosure is described below with reference to the drawings. The configuration of the embodiment described below is an example, and the present disclosure is not limited to the configuration of the embodiment. The present embodiment is described with reference to an exemplary case in which a reagent layer is formed using an ink-jet printer.

Figure 2:
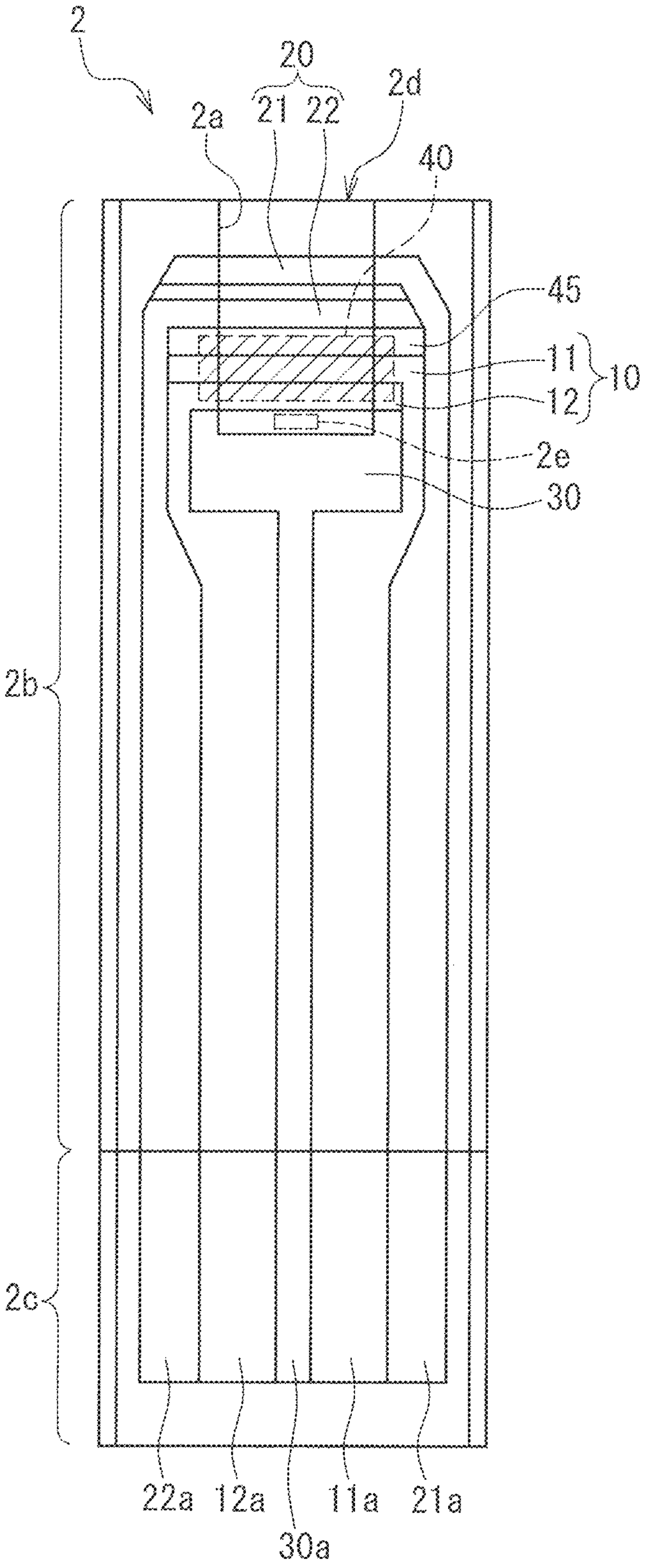
FIG. 2 is a schematic diagram for illustrating a schematic configuration of a biosensor in one embodiment of the present disclosure.

First, as illustrated in FIG. 2, an electrode system (conductive part) including a first electrode pair 10, a second electrode pair 20, and a blood-detection electrode 30 is formed on a base material by sputtering. The first electrode pair 10 includes a first working electrode 11 and a first counter-electrode 12, the second electrode pair 20 includes a second working electrode 21 and a second counter-electrode 22, and this electrode system is therefore composed of five electrodes.

Next, a reagent layer 40 is formed on the first electrode pair 10 (the first working electrode 11 and the first counter-electrode 12).

The reagent layer 40 can be formed by ejecting droplets of a reagent using an ink-jet printer. With the ink-jet printer, the reagent layer is formed on the conductive part by alternately repeating an ejection operation and a carrying operation. The ejection operation is an operation of ejecting a reagent liquid from a nozzle of the ink-jet head moving in an operation direction, and the carrying operation is an operation of carrying a base material in which the conductive part is formed by a predetermined distance. In addition, the ink-jet printer is capable of ejecting a reagent liquid from the nozzle, no matter which direction of the scanning direction (left and right directions) the ink-jet printer is moved. The time required for the carrying operation may be the drying time, or a time for a drying operation may be provided separately from the carrying operation.

The reagent layer 40 can be formed using a plurality of ink-jet printers. In such a manner that after the dot formation for the first layer is performed by a first ink-jet printer, the base material is carried to a second ink-jet printer where the dot formation for the second layer, the reagent layer, can be formed by layering dots of necessary layers (a required number of layers) by carrying the base material to the next ink-jet printer after dot formation. With this configuration, the time required for a carrying operation between ink-jet printers can be used for a drying operation.

The size of the reagent layer 40 in the present embodiment is set to a transverse direction (in the longitudinal direction of the biosensor 2) of 1000 μm, and a longitudinal direction (in the widthwise direction of the biosensor 2) of 2700 μm. The pitch for the ejection of droplets (distance between the center of the ejected droplet dot and the center of the next ejected droplet dot) is set to 70 μm, and the ejection of the reagent is performed 14 times (14 positions) in the transverse direction×39 times (39 positions) in the longitudinal direction.

The composition of ejected droplets (reagent liquid) can be appropriately determined depending on the reagent layer to be formed and the type of biosensor to be produced.

In one or a plurality of embodiments, the amount of the oxidoreductase in the reagent liquid is 1 KU/mL to 200

KU/mL. In one or a plurality of embodiments, the amount of the oxidoreductase in the reagent liquid is 5 KU/mL or more, 10 KU/mL or more, 15 KU/mL or more, 20 KU/mL or more, 25 KU/mL or more, or 30 KU/mL or more. In one or a plurality of embodiments, the amount of the oxidoreductase in the reagent liquid is 100 KU/mL or less, 90 KU/mL or less, 80 KU/mL or less, 70 KU/mL or less, 60 KU/mL or less, or 55 KU/mL or less.

In one or a plurality of embodiments, the amount of the electron transfer substance in the reagent liquid is 1 mM to 1000 mM. In one or a plurality of embodiments, the amount of the electron transfer substance in the reagent liquid is 2 mM or more, 5 mM or more, 10 mM or more, 50 mM or more, 100 mM or more, 200 mM or more, or 500 mM or more. In one or a plurality of embodiments, the amount of the electron transfer substance in the reagent liquid is 900 mM or less, 800 mM or less, or 700 mM or less.

In one or a plurality of embodiments, the amount of the buffer in the reagent liquid is 10 mM to 1000 mM. In one or a plurality of embodiments, the amount of the buffer in the reagent liquid is 20 mM or more, 50 mM or more, 100 mM or more, 150 mM or more, or 200 mM or more. In one or a plurality of embodiments, the amount of the buffer in the reagent liquid is 900 mM or less, 800 mM or less, 700 mM or less, 600 mM or less, or 500 mM or less.

In one or a plurality of embodiments, the amount of amino acid in the reagent liquid is 0.1 mass % to 20 mass % or 0.5 mass % to 10 mass %. In one or a plurality of embodiments, the amount of a surfactant in the reagent liquid is 0.1 mass % to 20 mass % or 0.5 mass % to 10 mass %.

In the formation of the droplet dot for the first layer, droplets of a reagent are ejected from a nozzle of an ink-jet head so that droplet dots having such a size that adjacent droplet dots do not overlap are formed. The ejected amount for a reagent for the first layer can be set to 10 ng to 18 ng (for example, 12 ng) per one droplet dot. In the case of this amount, it is possible to allow droplet dots ejected onto the conductive part to be maintained independent of one another, without uniting; that is, it is possible to prevent adjacent droplet dots from uniting and thereby forming one droplet.

After droplets of a reagent are ejected and droplet dots are formed, the droplet dots are dried. The drying of droplet dots can be performed at room temperature (humidity of 50% or less) for 20 seconds or more. This makes it possible to further reduce reagent irregularities and further enhance reproducibility. The size (in the major axis direction) of a dried droplet dot may be set to 50 μm to 70 μm.

Next, on the dried droplet dots of the first layer, droplet dots of the reagent for the second layer are formed.

Figure 3:
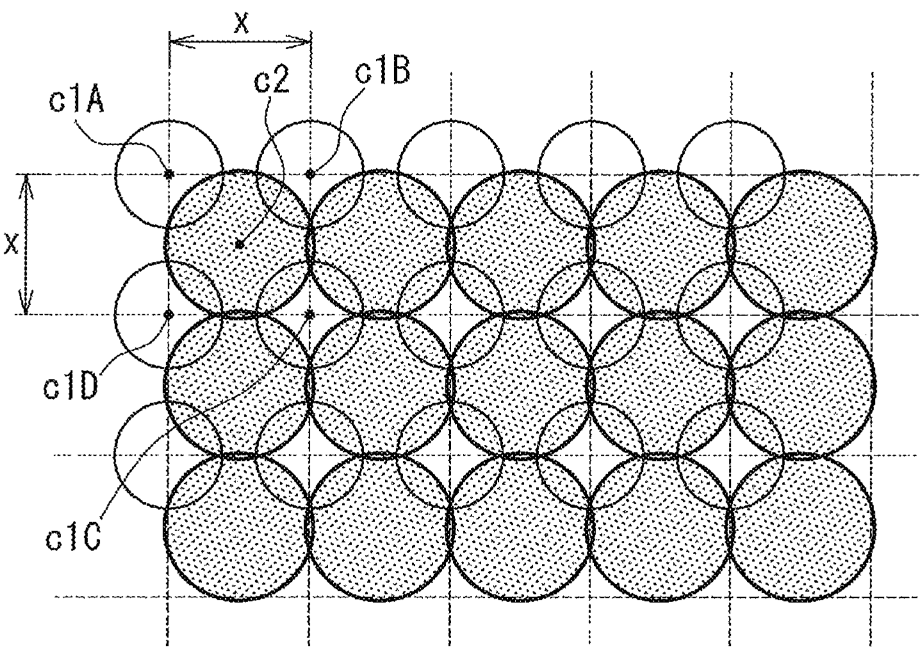
FIG. 3 is a schematic diagram for explaining a method of forming a reagent layer in an example.

In the formation of the droplet dots for the second layer, the position at which a reagent is ejected (the center of the droplet dot) is preferably a position where no droplet dot of the first layer is formed, for example, at a point of intersection of lines extended between the centers (for example, c1A, c1B, c1C, and c1D in FIG. 3) of adjacent dried droplet dots for the first layer (that is, at a point of intersection of diagonal lines of a quadrangle having the points of c1A, c1B, c1C, and c1D as vertices thereof) (at c2 in FIG. 3). Setting this position makes it possible to further reduce reagent irregularities, and further enhance reproducibility. Next, by ejecting droplets of the reagent on the dried droplet dots of the first layer, a part of the dried droplet dots of reagent for the first layer are dissolved, and the ejected droplets of reagent and the dissolved part of the dried droplet dots are dried together. This makes it possible to further reduce reagent irregularities and further enhance reproducibility.

In the formation of droplet dots for the second layer, droplets of the reagent are preferably ejected so that adjacent ejected droplets overlap. The ejected amount for a reagent for the first layer can be set to 20 ng to 28 ng (for example, 23 ng) per one droplet dot. With this amount, the dried droplet dot has a size (in the major axis direction) of 90 μm to 100 μm, whereby as shown in FIG. 3 the dried droplet dots (adjacent dried droplet dots) can overlap.

Next, on the dried droplet dots of the second layer, droplet dots of the reagent for the third layer are formed. The formation of droplet dots for the third layer can be performed in the same manner as that for the formation of the droplet dots for the second layer, except that the position at which a droplet is ejected (the center of the droplet dot) is set to the position at which the droplet was ejected for the first layer (the center of the droplet dot for the first layer). In the formation of droplet dots for the third layer, similarly, by ejecting droplets of the reagent on the dried droplet dots, a part of the dried reagent is dissolved, and the ejected droplet dots of the reagent and the dissolved part of the reagent are dried together. This makes it possible to further reduce reagent irregularities, and further enhance reproducibility.

Next, on the dried droplet dots of the third layer, droplet dots of the reagent for the fourth layer are formed. The formation of droplet dots for the fourth layer can be performed in the same manner as that for the formation of the droplet dots for the second or third layer except that the position at which a droplet is ejected (the center of the droplet dot) is set to the position at which the droplet was ejected for the second layer (the center of the droplet dot for the second layer).

In this way, the formation of droplet dots of the reagent is repeatedly performed in such a manner that, in the formation of droplet dots for an odd-numbered layer, the position at which a droplet is ejected (the center of the droplet dot) is set to the position at which the droplet was ejected for the first layer (the center of the droplet dot in the first layer), and in the formation of droplet dots for the even-numbered layer, the foregoing position is set to the position at which the droplet dot was ejected for the second layer (the center of the droplet dot in the second layer). Thereby, the reagent layer 40 can be formed.

In the formation of the reagent layer, similarly, dissolution of a part of the dried reagent (the dried reagent arranged on the base material) and the drying of the dissolved part of the dried reagent and the ejected droplet dots of the reagent are repeatedly performed, whereby reagent irregularities can be further reduced and the reproducibility can be further enhanced.

On the base material in which the reagent layer 40 is formed, a spacer (not shown) having a rectangular cutout part, as a cover area 2*b*, is arranged, and a cover (not shown) made of a synthetic resin in which an air hole 2*e* is formed, is arranged thereon, whereby a biosensor can be manufactured.

In one or a plurality of embodiments, the biosensor of the present disclosure can be used in a measuring device such as a blood glucose meter. An exemplary measuring device is shown in FIG. 1. The measuring device 1 shown in FIG. 1 can be used as a blood glucose meter such as a portable-type blood glucose measuring device, a self-monitoring blood glucose meter, or the like.

The measuring device 1 includes a main body 1*a*, as shown in FIG. 1. The main body 1*a* is provided with an insertion port 1*b* through which a biosensor 2 in a rectangular strip shape is inserted, a display screen 1*c* that displays measurement data, and a connector 1*d* for data communication with external equipment.

As illustrated in FIG. 1, a sample supply port 2*d* and an air hole 2*e* are formed in the biosensor 2. The sample supply port 2*d* communicates with a flow channel (2*a* in FIG. 2) to be described below. The air hole 2*e* is provided for discharging air in the flow channel (2*a* in FIG. 2), the air having come together with a sample supplied from the sample supply port 2*d* into the flow channel (2*a* in FIG. 2).

FIG. 2 illustrates a schematic diagram of one embodiment of a biosensor of the present disclosure. In FIG. 2, the upper side is the upstream side and the lower side is the downstream side.

The biosensor 2 includes a base material, a conductive part formed on the base material using a metal or carbon material, and a reagent layer 40 formed on the conductive part. On the conductive part and the reagent layer 40, a spacer (not shown) having a rectangular cutout part, as a cover area 2*b*, and further, on top of the same, a cover (not shown) made of a synthetic resin in which an air hole 2*e* is formed, are laminated. By laminating the base material, the spacer, and the cover, a space having the sample supply port 2*d*, formed by the cutout part of the spacer, is formed, and this space serves as the flow channel 2*a*. The air hole 2*e* is formed in the vicinity of the downstream end of the flow channel 2*a*.

In the present embodiment, the base material has a width of 7 mm, a length of 30 mm, and a thickness of 250 μm. The flow channel 2*a* has a width of 2 mm and a length of 4 mm. The reagent layer 40 has a length (in the widthwise direction of the biosensor) of 2.7 mm and a width (in the longitudinal direction of the biosensor) of 1 mm.

In the conductive part, the five electrodes, which are the first working electrode 11 and the first counter-electrode 12 as the first electrode pair 10, the second working electrode 21 and the second counter-electrode 22 as the second electrode pair 20, and the blood-detection electrode 30, are formed in such a manner that each of the electrodes is exposed in the flow channel 2*a*, in a rectangular shape, each parallel to the widthwise direction (lateral direction) of the biosensor 2. The first electrode pair 10, the second electrode pair 20, and the blood-detection electrode 30 exposed in the flow channel 2*a* are in contact with blood (sample) introduced therein, and function as a measurement area. Adjacent electrodes are insulated from each other. In a case where the conductive part is formed with a metal material formed by physical vapor deposition, predetermined electrode patterns are drawn by laser light (trimming) so that the electrodes are insulated from one another. In a case where the conductive part is formed with a carbon material, the electrodes are formed, separated at predetermined distances from one another. The conductive part (electrodes) of the present embodiment is formed with a nickel vanadium alloy.

Each electrode is extended along the longitudinal direction of the biosensor 2, and is bent in the widthwise direction of the biosensor 2 on the upstream end. These bending parts of the second working electrode 21, the second counter-electrode 22, the first working electrode 11, the first counter-electrode 12, and the blood-detection electrode 30 are positioned in parallel in the widthwise direction of the biosensor 2, in the stated order from the upstream side. Of each electrode, a portion thereof in the cover area 2*b* from the upstream end to the vicinity of the downstream end of the biosensor 2 is covered with the above-described cover (not shown), but a downstream end portion thereof is not covered but rather exposed, and this portion functions as a connector area 2*c* to be inserted into the insertion port 1*b* of the main body 1*a*. In this connector area 2*c*, a lead portion 11*a* of the first working electrode 11, a lead portion 12*a* of the first counter-electrode 12, a lead portion 21*a* of the second working electrode 21, a lead portion 22*a* of the second counter-electrode 22, and a lead portion 30*a* of the blood-detection electrode 30 are respective exposed contact points.

In the widthwise-direction middle part of the upstream portion of the biosensor 2, a gap is formed between each electrode and the cover (not shown). This gap is a capillary-type flow channel 2*a* through which blood containing a measurement object is introduced and flows, as described above. A non-conductive area 45 that is a gap between the second counter-electrode 22, which is the second electrode from the upstream side, and the first working electrode 11, which is the third electrode from the upstream side, is wider than the other gaps between the electrodes. This non-conductive area 45 is an area formed by laser light drawing rectangular patterns in the electrode layer, thereby being insulated from the other electrodes.

The reagent layer 40 is mounted on the first working electrode 11. As to the area where this reagent layer 40 is mounted, the downstream side thereof reaches the middle of the first counter-electrode 12, and the upstream side thereof reaches the middle of the non-conductive area 45 but does not reach the second counter-electrode 22. In other words, as the first working electrode 11 and the second counter-electrode 22 are separated by the non-conductive area 45, the reagent layer 40 mounted on the first working electrode 11 and the second counter-electrode 22 are prevented from coming into contact. When blood (sample) is spotted on the sample supply port 2*d* of the biosensor 2, the blood flows to the downstream side through the flow channel 2*a* by capillary force, from the second working electrode 21, the second counter-electrode 22, the first working electrode 11, the first counter-electrode 12, to the blood-detection electrode 30 in the stated order. Here, when the blood (sample) reaches the first working electrode 11, reagent components of the reagent layer 40 mounted on the first working electrode 11 are dissolved by the blood (sample).

An exemplary method of electrochemically measuring a measurement object in a sample using a biosensor 2 is described with reference to an exemplary case where the sample is whole blood and the measurement object is glucose.

First, the whole-blood sample is brought into contact with the sample supply port 2*d* of the biosensor 2. When the whole-blood sample is spotted on the sample supply port 2*d* of the biosensor 2, the blood flows to the downstream side through the flow channel 2*a* by capillary force, from the second working electrode 21, the second counter-electrode 22, the first working electrode 11, the first counter-electrode 12, to the blood-detection electrode 30 in the stated order. Here, when the whole-blood sample reaches the first working electrode 11, reagent components (oxidoreductase, electron transfer substance, etc.) contained in the reagent layer 40 mounted on the first working electrode 11 are dissolved by the whole-blood sample.

Then, when a positive potential is applied to the electrodes, electrons are transferred between the electron transfer substance present in the reagent layer 40 and the first working electrode 11 positioned below the reagent layer 40, and the oxidation current flows. Based on this, glucose concentration can be measured. In one or a plurality of embodiments, the voltage to be applied is 10 mV to 1000 mV, and preferably 100 mV to 600 mV.

The above-described embodiment is described with reference to, as an example, the configuration of the biosensor and the measuring method in a case where the sample is blood (for example, whole blood), but the present invention is not limited to this, and various biological specimens other than blood, such as urine, can be measured in the same manner.

The present disclosure may relate to one or a plurality of non-limiting embodiments described below:

[1] A biosensor comprising:

a base material;

a conductive part including two or more electrodes provided on a surface of the base material; and a reagent layer provided on at least a part of the conductive part, wherein the reagent layer is a reagent layer with the reagent stacked three-dimensionally, obtained by repeatedly forming droplet dots of a reagent on the conductive part.

[2] A method of manufacturing a biosensor, optionally the biosensor according to [1], wherein the biosensor comprises:

a base material;

a conductive part including two or more electrodes provided on a surface of the base material; and a reagent layer provided on at least a part of the conductive part, wherein the method including repeatedly forming droplet dots of a reagent on the conductive part to form the reagent layer in which the reagent is stacked three-dimensionally.

[3] The method according to [2], further including drying the droplet dots of the reagent.

[4] The method according to [2] or [3], further including:

forming droplet dots of the reagent for the Nth layer at predetermined pitches; and forming droplet dots of the reagent for the (N+1)th layer on the dried droplet dots of the Nth layer, wherein "N" is a natural number of 1 or greater.

[5] The method according to [4], wherein the formation of droplet dots of the reagent for the (N+1)th layer is performed so that the center of each of the droplet dots is positioned at a point of intersection of lines extended between centers of adjacent ones of the droplet dots in the Nth layer.

[6] The method according to [4] or [5], wherein the formation of droplet dots of the reagent for the (N+1)th layer is performed so that the droplet dots at least partially cover the dried droplet dots in the Nth layer.

[7] The method according to any one of [4] to [6], wherein the formation of droplet dots of the reagent for the first layer is performed so that adjacent ones of the droplet dots do not overlap.

[8] The method according to any one of [4] or [7], wherein the formation of droplet dots of the reagent for the second or subsequent layer is performed so that adjacent ones of the droplet dots abut one another.

[9] The method according to any one of [4] or [8], wherein the formation of droplet dots of the reagent is performed repeatedly until droplet dots of at least the fourth layer are formed.

[10] The method according to any one of [2] to [9], wherein the amount of a reagent is 10 ng to 30 ng per one droplet dot.

[11] The method according to any one of [2] or [10], wherein the formation of droplet dots is performed in such a manner that an amount for a reagent per one droplet dot for the first layer and that for the second or subsequent layer are different.

[12] The method according to any one of [2] to [11], wherein the formation of droplet dots of the reagent is performed until the mean thickness of the reagent layer is 5 μm to 10 μm.

[13] The method according to any one of [2] to [12], wherein a difference between a mean thickness of a peripheral part and a mean thickness of a central part in the reagent layer ([mean thickness of peripheral part]−[mean thickness of central part]) is −6 μm to +5 μm.

[14] The method according to any one of [2] to [13], wherein the reagent contains an oxidoreductase and an electron transfer substance.

[15] A biosensor manufactured by the method according to any one of [2] to [14].

[16] The biosensor according to [1], manufactured by the method according to any one of [2] to [14].

Hereinafter, although the following description describes the present disclosure in greater detail by way of examples, these are illustrative, and the present disclosure is not limited to these examples.

EXAMPLE

Example 1

A reagent layer was formed on a base material (PET, thickness 250 μm, length 30 mm×width 7 mm) on which electrodes were formed by dot-printing of a reagent using an ink-jet device in the following procedure. The formation of the reagent layer was performed under conditions of room temperature and a humidity of 50% or less.

<Procedure>

1. Reagent liquid was filled in a storage part of an ink-jet device, droplets of the reagent liquid (viscosity: 2 to 3 mPa·s) were ejected under the following conditions on the base material (made of PET) on which electrodes were formed, whereby liquid droplet dots (in a dotted pattern) were formed (the first layer). The amount of the reagent liquid ejected per one droplet was set to 12 ng (10 pL). The ejection pitch of the droplet (distance between the center of the ejected droplet dot and the center of the next ejected droplet dot) was set to 70 μm, and the ejection of the droplet dots was performed in a lattice pattern. After all of the droplet dots of the first layer were formed, the droplet dots were dried (30 seconds). The dried droplet dots had a diameter of 50 μm to 70 μm.

2. Next, on the dried droplet dots of the first layer, liquid droplet dots of the reagent were formed by ejecting liquid droplets of the reagent, and then dried (the second layer). The formation of the droplet dots for the second layer was performed in such a manner that the amount of the reagent liquid ejected per one droplet was set to 23 ng (18 pL), and the center of each ejected droplet dot was positioned at an approximate center (c2 in FIG. 3) of a square having vertices at the centers (c1A, c1B, c1C, and c1D in FIG. 3) of adjacent ones of the droplet dots of the first layer. The dried droplet dots of the second layer had a diameter of 90 μm to 100 μm. In the formation of the droplet dots for the second layer, the ejection pitch of the droplet (distance between the centers of the ejected dot and the centers of the next ejected droplet dot) was set to 70 μm, as in the first layer.

3. Next, on the dried droplet dots of the second layer, liquid droplet dots of the reagent were formed by ejecting liquid droplets of the reagent, and then dried (the third layer). The formation of the droplet dots for the third layer was performed in such a manner that the amount of the reagent liquid ejected per one droplet was set to 23 ng, and the centers of the droplet dots were positioned at approximately the same positions as the centers of the droplet dots of the first layer.

4. Next, droplet dots of the reagent for the fourth layer were formed on top of the dried droplet dots of the third layer. The formation of the droplet dots for the fourth layer was performed in the same manner as that for the second layer.

5. Next, droplet dots of the reagent for the fifth layer were formed on top of the dried droplet dots of the fourth layer. The formation of the droplet dots for the fourth layer was performed in the same manner as that for the third layer. Through these procedures, the three-dimensionally layered reagent layer (an approximate rectangular parallelepiped (quadrangular prism)) was obtained. The amount of FAD-dependent Glucose Dehydrogenase in the obtained reagent layer was 232 KU/$cm^3$, and the amount of the electron transfer substance was 3.56 mmol/$cm^3$.

<Conditions for Formation of Droplet Dots>

Distance between the centers of adjacent dots (for example, distance (X) between c1A and c1B in FIG. 3): 70 μm Number of times of ejection: 14 times in the transverse direction×39 times in the longitudinal direction, to the reagent layer formation area (transverse: 1000 μm, longitudinal: 2700 μm, rectangular parallelepiped)

The composition of the reagent liquid was as follows.

<Composition of Reagent Liquid>

FAD-dependent Glucose Dehydrogenase (product name: Glucose Dehydrogenase "Amano" 8, MW: 180,000, manufactured by Amano Enzyme Inc.): 48 KU/mL Ru complex ($Ru(NH_3)_6Cl_3$, manufactured by LT Metal Co. Ltd.): 626 mM 1-Methoxy PES (1-methoxy-5-ethylphenazinium ethylsulfate, manufactured by Dojindo Laboratories Co., Ltd.): 2.27 mM Phosphate buffer (pH 7.0): 300 mM Glycine: 2 mass %

CHAPS: 2 mass %

Antifoam agent: 0.04 mass %

[Measurement of Size of Dried Droplet Dot]

The sizes of dried droplet dots were measured by a digital microscope (VHX-6000, manufactured by Keyence Corporation).

Figure 5:
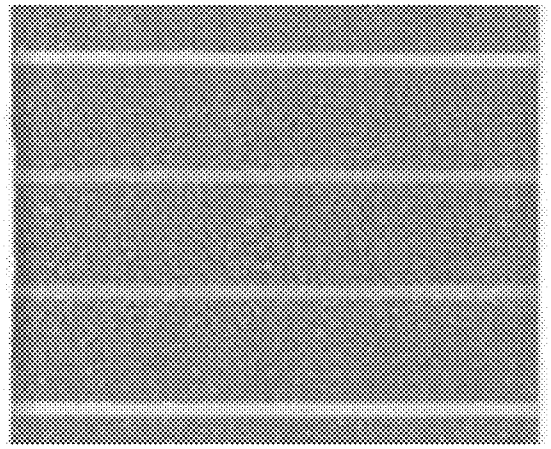
FIG. 5 illustrates an exemplary photograph of the reagent layer formed in the example.

The obtained photograph of the reagent layer is shown in FIG. 5. White lines in FIG. 5 are laser-printed lines for setting boundaries of respective electrodes of the conductive part in contact with the bottom of the reagent layer. As shown in FIG. 5, the reagent layer formed by the method of the present disclosure was uniform, with the reagent irregularities being suppressed. It is considered that alternately repeating the dropping of a very small amount of reagent and the drying prevents shifting of a reagent within a reagent formation area from occurring upon redissolution.

[Measurement of Thickness of Reagent Layer]

The thickness of the obtained reagent layer was measured using a benchtop stylus profiling system (product name: DektakXT, manufactured by BRUKER). The measurement was performed along the center line of the reagent layer along the transverse direction of the reagent layer (the center line along the longitudinal direction of the biosensor, the center line passing the position of approximately 1350 μm from the left end) (in the arrow direction in FIG. 6). The reagent layer has a rectangular shape when viewed from above the top surface.

<Mean Thickness>

The height (the thickness of the reagent layer) was measured in increments of 670 nm, from one end to the other end (from the upstream side to the downstream side of the biosensor) along the center line of the reagent layer (at the position of approximately 1,350 μm from the left end) in the transverse direction of the reagent layer. By calculating an arithmetic mean of the measured values, the mean thickness of the reagent layer was measured.

<Difference Between Mean Thickness of Peripheral Part and Mean Thickness of Central Part in Reagent Layer>

Using the thicknesses of the reagent layer measured as described above, a mean thickness ($TH_{EN}$) of both end parts and a mean thickness ($TH_{EC}$) of the central part were calculated. The mean thickness ($TH_{EN}$) of both end parts was calculated by determining an arithmetic mean of the thicknesses of both end parts (the upstream side and the downstream side of the biosensor) ($EN_1$ and $EN_2$ in FIG. 4, each with a width of 0.1 mm). The mean thickness ($TH_{CE}$) of the central part was calculated by determining an arithmetic mean of the thicknesses in a range with a width of 0.2 mm around the point of intersection of the transverse-direction center line and the longitudinal-direction center line in the reagent layer. In other words, it is the mean value of thicknesses in a range with a width of 0.1 mm on each side from the point of intersection (on the upstream side and the downstream side) along the center line in the transverse direction of the reagent layer (CE in FIG. 4, a range with a width of 0.2 mm in total). With the mean thickness of both end parts (the mean thickness ($TH_{EN}$) of the peripheral part) and the mean thickness ($TH_{CE}$) of the central part thus obtained, the difference between mean thicknesses of the peripheral and central parts of the reagent layer was determined by the following equation:

$$[\text{Difference between mean thicknesses of peripheral and central parts}]=(TH_{EN})-(TH_{CE})$$

[Reproducibility Test of Glucose Current Value]

A glucose current value reproducibility test was performed using the biosensor in which the reagent layer was formed by the above-described method. The reproducibility of glucose current value was defined as a mean of glucose current values at respective sample concentrations (Cyclic Voltammetry, C.V.).

Figure 8:
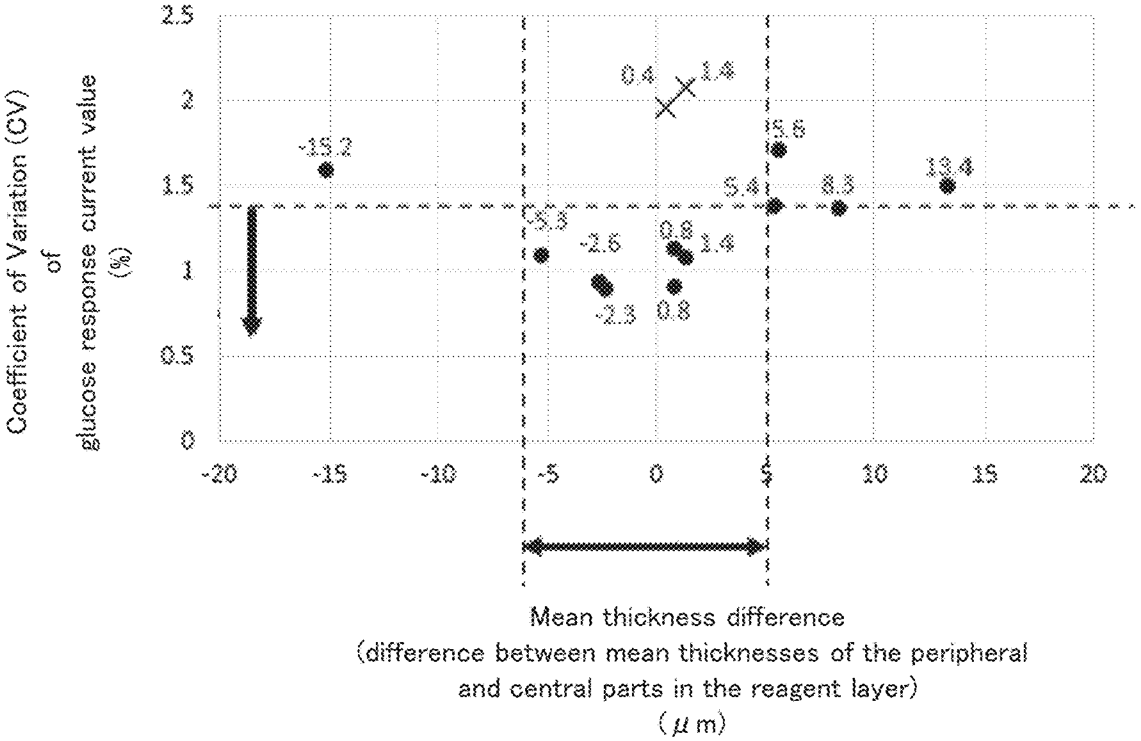
FIG. 8 illustrates exemplary results obtained in the example, which show the relationship between the coefficient of variation (CV) (%) (reproducibility of glucose response current value), and the difference between mean thicknesses of the peripheral and central parts in the reagent layer.

A potentiostat (manufactured by Arkray Inc.) was used, and a voltage was applied at 0.2 V to measure current values. A coefficient of variation (CV) (%) was determined from the determined current values. The results are shown in FIG. 8.

A lower C.V. means high reproducibility, and a CV of less than 1.4 indicates the preferred reproducibility for the biosensor.

<Evaluation Conditions>

Used sample: Whole-blood sample

Glu/Hct concentration: Glu45 mg/dl/Hct42%, Glu130 mg/dl/Hct42%, Glu330 mg/dl/Hct42%

The number of evaluations: n=10 (as the evaluations were performed at each Glu/Hct concentration, 30 evaluations in total were carried out)

Figure 7:
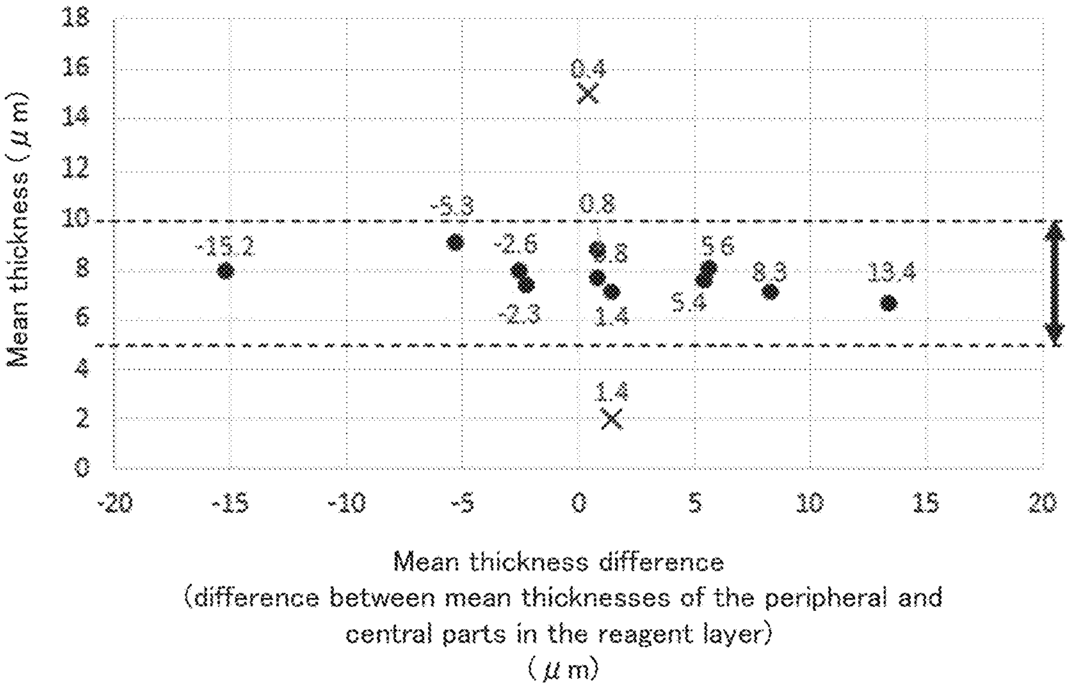
FIG. 7 illustrates exemplary results obtained in the example, which show the relationship between the mean thickness and the difference between mean thicknesses of the peripheral and central parts in the reagent layer.

FIG. 7 shows the relationship between the mean thickness and the difference between mean thicknesses of the peripheral and central parts (mean thickness difference) in the obtained reagent layer, and FIG. 8 shows the relationship between the CV (%) of glucose response current value (the reproducibility of glucose response current value) and the difference between mean thicknesses of the peripheral and central parts. The values shown in the graphs of FIGS. 7 and 8 are differences between the mean thicknesses of the peripheral and central parts (mean thickness difference) in the respective reagent layers. In FIG. 7, data of mean thicknesses of the reagent layer in a range of 5 μm to 10 μm are plotted by marks of "black circle," and data outside the range of 5 μm to 10 μm are plotted by marks of "x." In FIG. 8, in data showing the difference between the mean thickness of the peripheral and central parts falling in a range of −6 μm to +5 μm, data of the Glu value reproducibility (%) of less than 1.4% are plotted by marks of "black circle", and data of 1.4% or more are plotted by marks of "x."

As shown in FIGS. 7 and 8, the mean thickness of the reagent layer (height of reagent) was 5 μm to 10 μm, and when the difference between mean thicknesses of the peripheral and central parts (height difference) was −6 μm to +5 μm, CV (%) was less than 1.4%, lot-to-lot differences and within-lot differences were reduced, and a high reproducibility was obtained.

Example 2

A reagent layer was formed in the same manner as that of Example 1 except that droplet dots of the first layer to the fifteenth layer were formed by repeatedly performing the formation of droplet dots. The formation of droplet dots for the odd-numbered layers other than the first layer (the third, fifth, seventh, ninth, eleventh, thirteenth, and fifteenth layers) was performed in the same manner as that for the third layer of Example 1. The formation of droplet dots for the even-numbered layers (the second, fourth, sixth, eighth, tenth, twelfth, and fourteenth layers) was performed in the same manner as that for the second layer of Example 1. A photograph of the reagent layer obtained is shown in FIG. 9.

Figure 9:
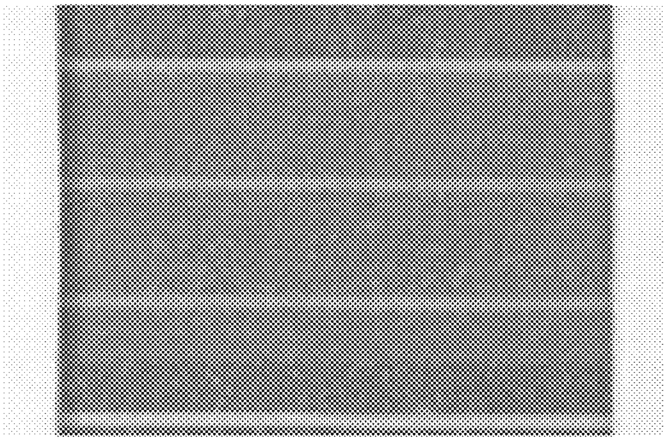
FIG. 9 illustrates an exemplary photograph of the reagent layer formed in the example.

As shown in FIG. 9, the reagent layer formed by the method of the present disclosure was uniform, with the reagent irregularities being suppressed.

The disclosure may be embodied in other forms without departing from the spirit or essential characteristics thereof. The embodiments disclosed in this application are to be considered in all respects as illustrative and not limiting. The scope of the disclosure is indicated by the appended claims rather than by the foregoing description, and all changes that come within the meaning and range of equivalency of the claims are intended to be embraced therein.

What is claimed is:

1. A biosensor, comprising:

a base material;

a conductive part including two or more electrodes provided on a surface of the base material; and a reagent layer provided on at least a part of the conductive part, wherein the reagent layer includes a plurality of dot layers that are stacked three-dimensionally, each of the plurality of dot layers being made of droplet dots of a reagent, the plurality of dot layers includes a first dot layer and a second dot layer, the first dot layer is configured such that each droplet dot of the first dot layer is spaced apart from the other droplet dots of the first dot layer, and the second dot layer, directly formed on the first dot layer, is configured such that each droplet dot of the second dot layer directly contacts two or more droplet dots of the second dot layer.

2. A biosensor according to claim 1, wherein the second dot layer is configured such that each droplet dot of the second dot layer directly contacts three or more droplet dots of the second dot layer.

3. A biosensor according to claim 1, wherein the plurality of dot layers further includes a third dot layer, and the third dot layer is configured such that each droplet dot of the third dot layer overlaps, in a plan view of the reagent layer, a corresponding droplet dot of the second dot layer.

4. A biosensor according to claim 1, wherein the plurality of dot layers includes at least four dot layers.

5. A method of manufacturing a biosensor, wherein the biosensor comprises:

a base material;

a conductive part including two or more electrodes provided on a surface of the base material; and a reagent layer provided on at least a part of the conductive part, wherein the method comprises repeatedly forming a plurality of dot layers on the conductive part to form the reagent layer in which the plurality of dot layers are stacked three-dimensionally, each of the plurality of dot layers being made of droplet dots of a reagent, wherein the plurality of dot layers includes a first dot layer and a second dot layer, and the formation of the reagent layer includes:

forming droplet dots of the reagent for the first dot layer such that each droplet dot of the first dot layer is spaced apart from the other droplet dots of the first dot layer; and forming droplet dots of the reagent for the second dot layer directly on the first dot layer after formation of the first dot layer, such that each droplet dot of the second dot layer directly contacts two or more droplet dots of the second dot layer.

6. The method according to claim 5, further comprising drying the droplet dots of the reagent.

7. The method according to claim 5, further comprising:

forming droplet dots of the reagent for an Nth dot layer at a predetermined pitch; and forming droplet dots of the reagent for an (N+1)th dot layer on the Nth dot layer after the Nth dot layer is dried, wherein N is a natural number greater than or equal to 1.

8. The method according to claim 7, wherein the formation of droplet dots of the reagent for the (N+1)th dot layer is performed so that the center of each of the droplet dots is positioned at a point of intersection of lines extended between the centers of adjacent ones of droplet dots in the Nth dot layer.

9. The method according to claim 7, wherein the formation of droplet dots of the reagent for the (N+1)th dot layer is performed so that the droplet dots at least partially cover the dried droplet dots in the Nth dot layer.

10. The method according to claim 7, wherein the formation of droplet dots of the reagent is performed repeatedly until droplet dots of at least a fourth dot layer are formed.

11. The method according to claim 5, wherein the amount of a reagent is 10 ng to 30 ng per one droplet dot.

12. The method according to claim 5, wherein the formation of droplet dots is performed in such a manner that an amount for a reagent per one droplet dot for the first dot layer and that for the second or subsequent dot layers are different.

13. The method according to claim 5, wherein the formation of droplet dots of the reagent is performed until the mean thickness of the reagent layer is 5 μm to 10 μm.

14. The method according to claim 5, wherein a difference between a mean thickness of a peripheral part and a mean thickness of a central part in the reagent layer is −6 μm to +5 μm

[mean thickness difference]=[mean thickness of peripheral part]−[mean thickness of central part].

15. The method according to claim 5, wherein the reagent contains an oxidoreductase and an electron transfer substance.

16. The method according to claim 5, wherein forming the droplet dots of the reagent for the second dot layer includes forming the droplet dots such that each droplet dot of the second dot layer directly contacts three or more droplet dots of the second dot layer.

17. The method according to claim 5, wherein the plurality of dot layers further includes a third dot layer, and the formation of the reagent layer further includes forming droplet dots of the reagent for the third dot layer such that each droplet dot of the third dot layer overlaps, in a plan view of the reagent layer, a corresponding droplet dot of the second dot layer.

* * * * *